(12) United States Patent
Shah et al.

(10) Patent No.: US 10,751,285 B1
(45) Date of Patent: Aug. 25, 2020

(54) SYNTHESIS OF C RESORCINARENE BASED NOVEL AMPHIPHILIC SUPRAMOLECULAR MACROCYCLE AS NANO-SCALE DRUG LOADING SYSTEM

(71) Applicants: Muhammad Raza Shah, Karachi (PK); Imdad Ali, Karachi (PK); Heyam Saad Ali, Dubai (AE); Babiker M. El-Haj, Dubai (AE); Muhammad Imran, Karachi (PK)

(72) Inventors: Muhammad Raza Shah, Karachi (PK); Imdad Ali, Karachi (PK); Heyam Saad Ali, Dubai (AE); Babiker M. El-Haj, Dubai (AE); Muhammad Imran, Karachi (PK)

( * ) Notice: Subject to any disclaimer, the term of this patent is extended or adjusted under 35 U.S.C. 154(b) by 0 days.

(21) Appl. No.: 16/412,252

(22) Filed: May 14, 2019

(51) Int. Cl.
*A61K 9/127* (2006.01)
*A61K 31/351* (2006.01)

(52) U.S. Cl.
CPC .......... *A61K 9/1277* (2013.01); *A61K 31/351* (2013.01)

(58) Field of Classification Search
CPC .............................. A61K 9/127; A61K 31/351
See application file for complete search history.

(56) References Cited

PUBLICATIONS

Ali et al. (Chem. Eur. J. 2013, 19, 12938-12942).*
Wang et al. Chem. Eur. J. 2013, 19, 12938-12942.*

* cited by examiner

*Primary Examiner* — Shirley V Gembeh
(74) *Attorney, Agent, or Firm* — Sarfaraz K. Niazi

(57) ABSTRACT

A drug delivery system comprising the synthesis of resorcinarene based novel amphiphilic supramolecular macrocycle that is capable of self-assembling in nano-scale vesicles upon its contact with aqueous medium and its use as nano-drug loading vehicle when mixed with cholesterol (2:1 ratio w/w).

2 Claims, 4 Drawing Sheets

SYNTHESIS OF C RESORCINARENE BASED NOVEL AMPHIPHILIC SUPRAMOLECULAR MACROCYCLE AS NANO-SCALE DRUG LOADING SYSTEM

FIELD OF INVENTION

The current invention describes the synthesis of resorcinarene based novel amphiphilic supramolecular macrocycle that self-assembles in nano-scale vesicles upon its contact with aqueous medium and its use as nano-drug loading system when mixed with cholesterol (2:1 ratio w/w).

BACKGROUND OF INVENTION

Efficacy and safety of therapeutic agents can be improved through nano-scale drug delivery systems. Nano-scale drug delivery systems localize drugs in the target tissues in increased amount, increase the drugs stability and permeability across the biological membranes, thus improving their bioavailability and therapeutic efficacy.

Vesicles and micelles based nano drug delivery systems are preferred due to their demonstrated advantages such as unique and diverse structural features, increased drug loading, drugs protection from degradation and ultimately increase in bioavailability of their loaded drugs.

Nano-range vesicular drug carriers are highly biocompatible, biodegradable and are currently getting wider attention amphiphilic nature, biodegradability and ability to carry both hydrophilic and liphophilic drugs. Similarly, their size, shape and lamellarity can be controlled, thus leading to protection of their loaded contents against enzymatic and chemical degradation which in turn improves their therapeutic effects.

Till now, many molecules have been investigated for designing nanocarriers based drug delivery systems. Supramolecular amphiphiles based nano drug delivery systems are preferred due to their multiple versatile properties such as formation of various nano structures upon their spontaneous aggregation. Similarly, upon application of certain stimulus, supramolecular based nano drug delivery systems undergo phase transitions which results in on-demand drug release.

Supramolecular amphiphiles provide a "host-guest" relationship for the hydrophobic drugs by accommodating them in their cavities on molecular levels. This leads to prolonged and sustained release of the guest drugs over a longer time. Macrocycles based supramolecular hosts have got increasing interest for nano drug delivery systems and they have been the precursors for the synthesis of various novel biomedical materials owing to their natural supramolecular self-assembly.

During last three decades, various macrocycles have been synthesized for drug delivery applications. They include crown ethers, catenanes, cyclophanes, cucurbiturils, cryptophanes, calixarenes, porphyrins and carcerands. Nano drug delivery systems based on these macrocycles are able to reduce the drug side effects and improve their pharmacokinetics; yet maximum therapeutic benefits cannot be achieved for the delivered drugs. Thus synthetic scientists are in search of novel supramolecular macrocycles with unique physico-chemical properties for constructing efficient nano drug delivery systems.

The present study reports the synthesis of resorcinarene based a novel amphiphilic supramolecular macrocycle. The synthesis of the amphiphilic supramolecular macrocycle was achieved through two step reaction. In first step, 4-hydroxybenzaldehyde was derivitized with 1-bromohexadecane to get lipophilic intermediate product. In next step, intermediate product was reacted with resorcinol in the presence of acetic acid and sulphuric acid and under the optimized reaction conditions to get amphiphilic supramolecular macrocycle (ASRM) as shown in Scheme 1.

The synthesized amphiphilic supramolecular macrocycle was investigated for its critical micelles concentration (CMC) through UV-visible spectrophotometer.

The synthesized novel amphiphilic supramolecular macrocycle (ASRM) was investigated for its ability of self-assembling in nano-range vesicles in aqueous medium in combination with cholesterol (2:1 ratio w/w).

The drug loading capabilities of the synthesized novel amphiphilic supramolecular macrocycle (ASRM) were explored nano-range vesicles following thin file re-hydration method using Amphotericin B as model hydrophobic drug.

The synthesized amphiphilic supramolecular macrocycle (ASRM) was capable of forming nano-size vesicles upon its self-assembling in aqueous medium and loaded increased concentration of the model hydrophobic drug.

BRIEF SUMMARY OF THE INVENTION

This invention relates to the synthesis of resorcinarene based novel amphiphilic supramolecular macrocycle which is used as drug loading and carrier molecule upon its self-assembling in nano-size vesicles in aqueous medium in combination with cholesterol.

The synthesis of the novel amphiphilic supramolecular macrocycle was achieved through two step reaction. A lipophilic intermediate product was synthesized by reacting 4-hydroxybenzaldehyde with 1-bromohexadecane. In next step, lipophilic intermediate product was reacted with resorcinol in the presence of acetic acid and sulphuric acid and under the optimized reaction conditions to get amphiphilic supramolecular macrocycle (ASRM).

The synthesized novel amphiphilic supramolecular macrocycle was investigated for its CMC in methanol.

The resultant synthetic novel amphiphilic supramolecular macrocycle was investigated for its ability of self-assembling in nano-range vesicles in aqueous medium in combination with cholesterol (2:1 ratio w/w).

The synthetic novel amphiphilic supramolecular macrocycle was explored for the very first time for its self-assembling in aqueous medium in combination with cholesterol and for its drug loading and delivering applications.

The nano-size vesicles of the novel amphiphilic supramolecular macrocycle loaded increased amount of the model hydrophobic Amphotericin B.

DETAILED DESCRIPTION OF THE INVENTION

An intermediate product was synthesized by adding 610 mg (5 mmol) of 4-hydroxybenzaldehyde with 690 mg (5 mmol) $K_2CO_3$ in 25 mL acetone and refluxed at 80° C. for 40 min. This was followed by addition of 1.53 mL (5 mmol)

1-bromohexadecane to the reaction mixture and refluxed for 12 h. The reaction was monitored by thin layer chromatography (TLC), using ethyl acetate and n-hexane (1:9) as solvent system. The organic portions were collected, combined, dried with $MgSO_4$ and rotary evaporated to get crude product. Pure white solid intermediate product was obtained by subjecting the crude product to silica-gel column purification with n-hexane as eluent.

In second step, 440 mg (4 mmol) resorcinol and 1392 mg (4 mmol) of 4-HBA were added to 40 mL acetic acid in 100 mL round bottom flask and stirred for 20 min. This was followed by the addition of 0.5 mL sulphuric acid to the reaction mixture and refluxed at 80° C. for 24 h. After 24 h, the reaction mixture was placed in ice-bath; brown precipitate of ASRM was filtered, washed thoroughly with cold water and dried.

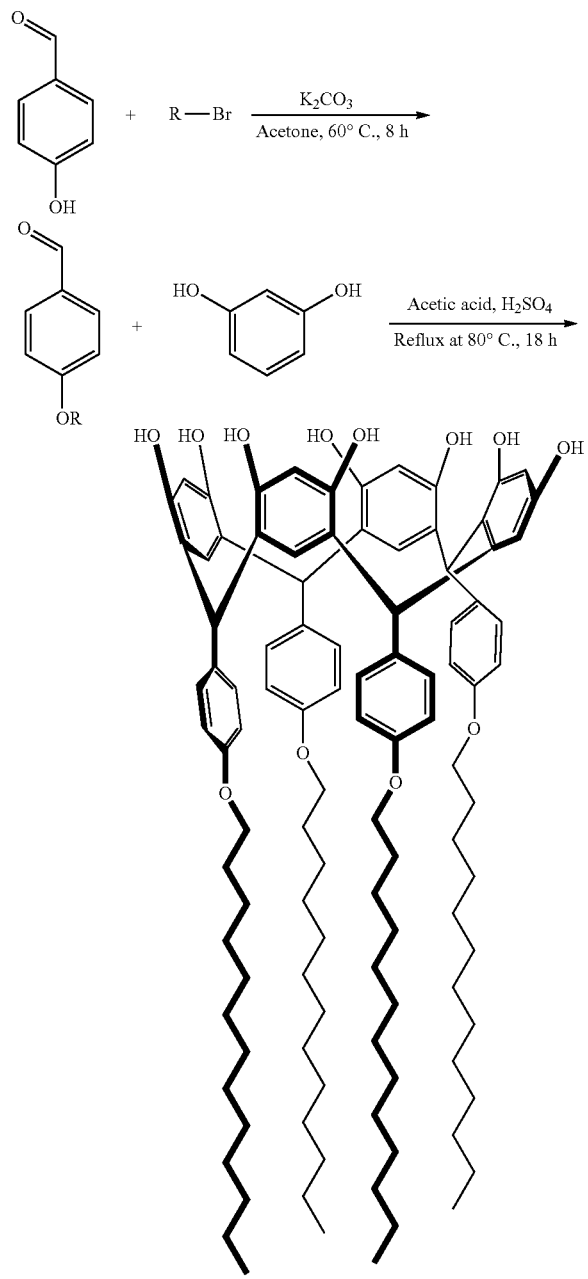

Scheme-1: Synthesis Scheme for Supramolecular Amphiphilic Macrocylce (ASRM)

The synthesis of novel resorcinarene based amphiphilic supramolecular macrocycle was confirmed through Mass and $^1HNMR$ spectroscopic techniques.

Figure 3:
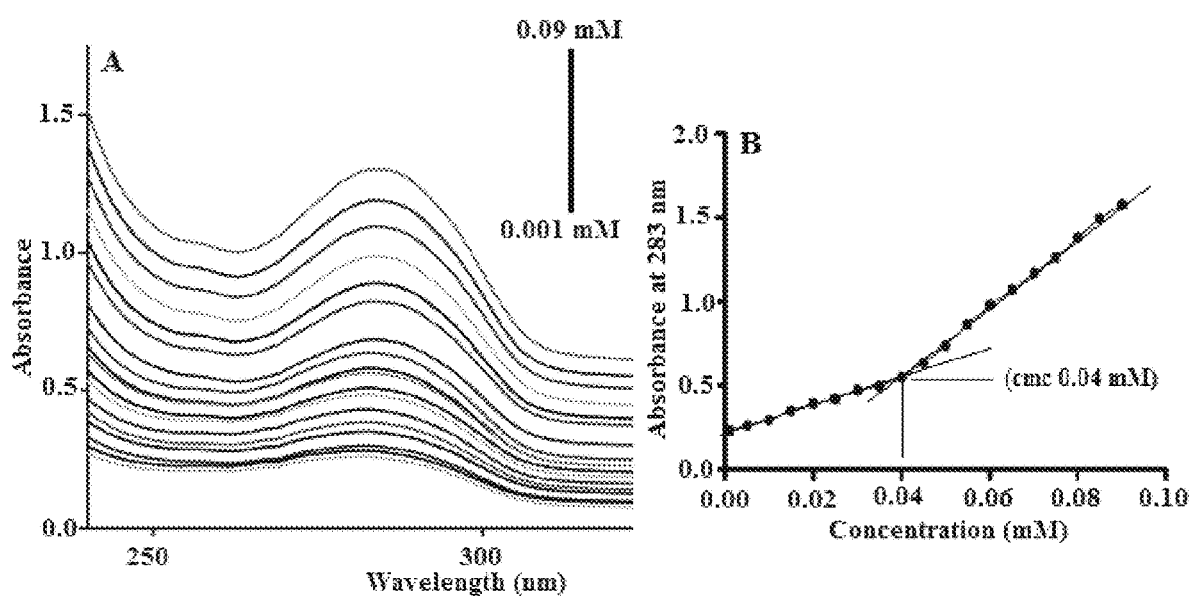
FIG. 3 depicts (A) UV-vis spectrum of ASRM and (B) CMC of ASRM

CMC of the synthesized resorcinarene based amphiphilic supramolecular macrocycle was investigated in methanol using UV-visible spectrophotometer. Amphiphile methanolic solutions in 0.001-0.09 mM range were read on UV-visible spectrophotometer, giving characteristic absorbance at 283 nm. Absorbance was plotted against respective concentration and CMC of the novel synthesized amphiphile was found to be 0.04 mM as shown in FIG. 3.

The synthesized resorcinarene based amphiphilic supramolecular macrocycle was investigated for its self-assembling in nano-size vesicles and drug loading using Amphotericin B as model hydrophobic drug.

Drug loaded nano-size vesicles of novel synthesized resorcinarene based amphiphilic supramolecular macrocycle were obtained using thin film re-hydration method. Briefly, novel synthesized resorcinarene based amphiphilic supramolecular macrocycle (100 mg), cholesterol (50 mg) and model hydrophobic drug Amphotericin B (50 mg) were dissolved in 30 mL mixed solvent system of tetrahydrofuran and methanol (6:4, v/v). All the organic solvents were evaporated through rotary evaporator and resulting thin lipid film was further dried under reduced pressure. The thin film was hydrated with distilled water at 60° C. for 30 min. The re-hydration of the thin film resulted in the formation of drug loaded vesicles which were further reduced by sonication in ultrasonicator.

The nano-vesicles of novel synthesized resorcinarene based amphiphilic supramolecular macrocycle were investigated for their Amphotericin B loading efficiency using HPLC. Amphotericin B loaded nano-vesicles were centrifuged for 20 min at 12,000 rpm. The supernatant containing free drug was diluted in specific mobile phase and resulting solution was run on HPLC using respective mobile phase and chromatographic conditions. Results revealed that nano-vesicles of novel synthesized resorcinarene based amphiphilic supramolecular macrocycle were capable of loading 92.05±4.39% Amphotericin B (n=3).

Figure 4:
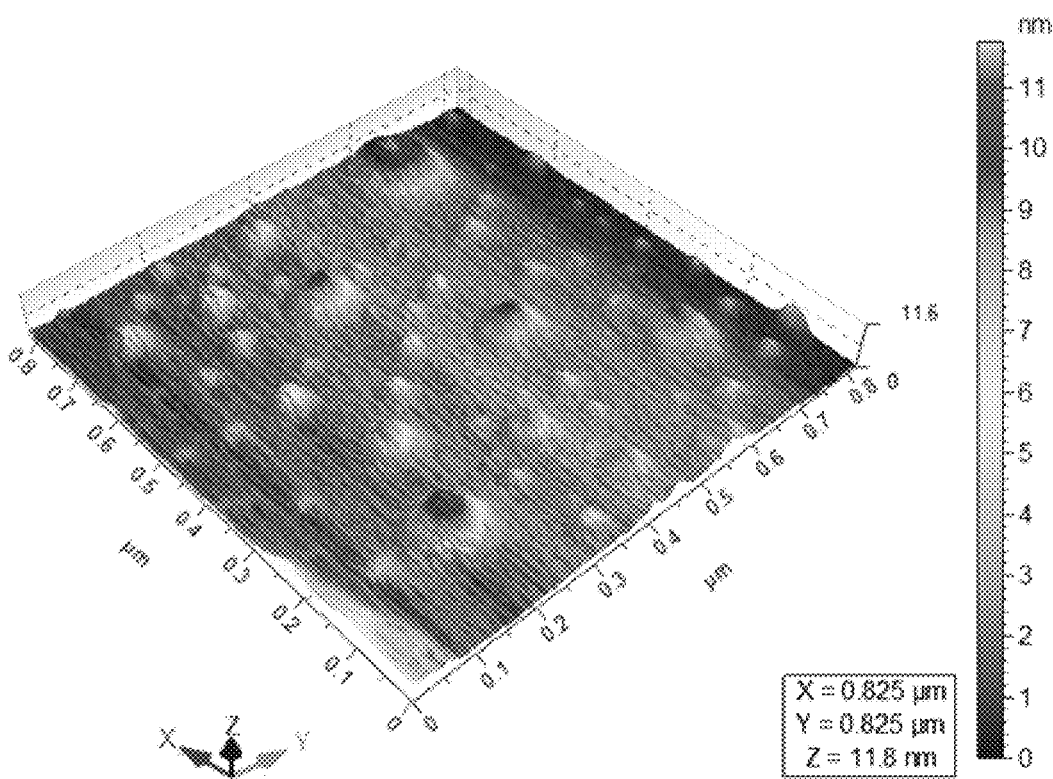
FIG. 4 depicts atomic force microscope (AFM) images revealing the self-assembling of the synthesized novel supramolecular amphiphilic macrocylce (ASRM) into nano-size vesicles in aqueous medium.

Amphotericin B loaded nano-vesicles of novel synthesized resorcinarene based amphiphilic supramolecular macrocycle were also investigated for shape, size, size distribution and surface charge or zeta potential using zetasizer. The vesicles were found in nano-size range revealing a mean diameter of 174.4±3.78 nm (n=3). The vesicles seemed to be nearly homogeneous in size as indicated by their polydispersity index (0.12±0.10, n=3). The vesicles were found to a negative surface charge of −5.77±2.51 mV (n=3). Atomic force microscope (AFM) analysis showed the vesicles to be spherical in shape as shown in FIG. 4.

Results justify the use of the synthesized resorcinarene based novel amphiphilic supramolecular macrocycle as an efficient material for designing of nano-scale vesicular drugs loading system.

Figure 1:
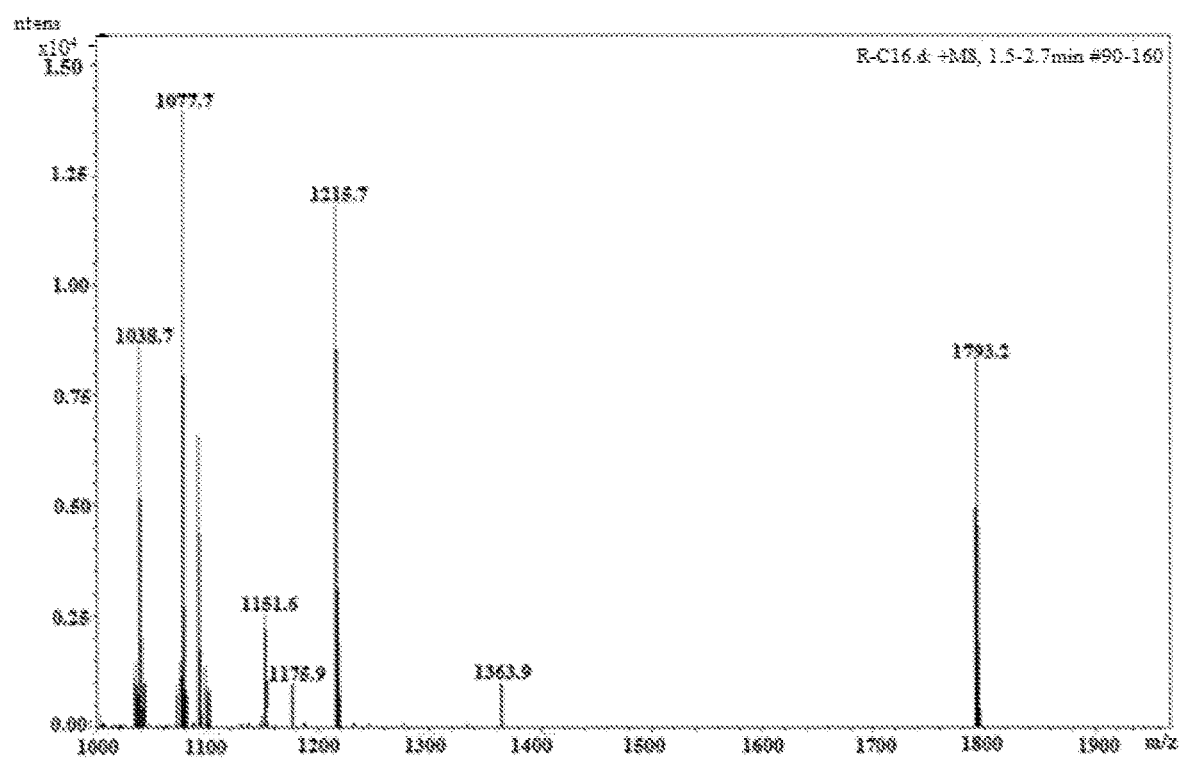
FIG. 1 depicts the Mass Spectrum of the synthesized novel supramolecular amphiphilic macrocylce (ASRM).
Figure 2:
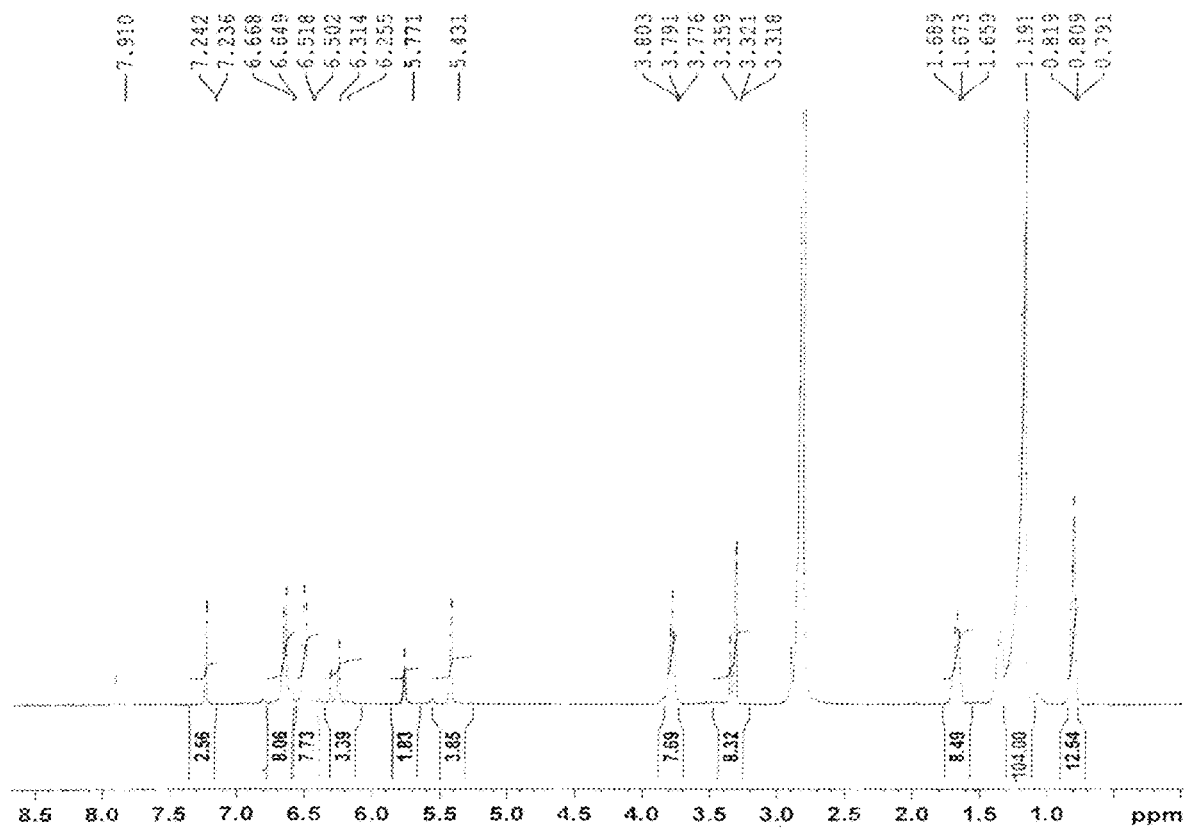
FIG. 2 depicts the $^1$H NMR spectra of the synthesized novel supramolecular amphiphilic macrocylce (ASRM).

Yield 1530 mg; 87.27%, m.p; 168-178° C.; MS (MALDI-TOF, m/z):1793.2; $^1H$ NMR (400 MHz, $CDCl_3$) δ:0.79 (t, 12H, $CH_2$, J=7.2 Hz), 1.19 (m, $CH_2$, 104H), 1.65 (t, 8H, $CH_2$, J=5.6 Hz), 3.31 (t, 8H, $CH_2$, J=4 Hz), 3.77 (t, 8H, OH, J=6 Hz), 5.43 (s, 4H, CH), 6.25 (d, 4H, CH), 6.50 (d, 8H, CH, J=6.4 Hz), 6.64 (d, 8H, CH, J=7.6 Hz), 7.23 (s, 2H, CH); IR (KBr, $cm^{-1}$) 3617.7 (—OH), 2930.9 ($CH_3$), 2852.3 ($CH2$), 1640.4 (C=C aromatic), 1153.4 (C—O ether). Novel amphiphile (ASRM) shows 1753.3 as theoretical calculated mass which is confirmed by ESI-MS spectrum showing 1793.2 m/z [M+K]$^+$. Increase in experimental mass can be due to addition of potassium ion as shown in FIG. 1. $^1$HNMR spectrum (FIG. 2) of novel amphiphile shows a triplet of 12 methyl protons attached to terminal carbons of the aliphatic chains at 0.80 ppm. A multiplet of remaining CH$_2$ groups in aliphatic chain (104H) appeared at 1.19 ppm, a triplet peak with 8H of four methylene groups is observed at 1.67 ppm while a triplet peak of 8 protons of CH$_2$ groups was appeared at 3.31 ppm. A singlet peak is observed at 3.77 ppm with 8H of hydroxyl groups attached to aromatic rings and a singlet peak for aromatic CH (4H) was observed at 5.43 ppm. A doublet peak for 4 protons appeared at 6.25 ppm of aromatic CH, at 6.50 ppm a doublet peak of aromatic ring 8Hand a doublet of other 8 aromatic protons was observed at 6.64 ppm. A doublet peak at 7.23 ppm was observed for 4H of aromatic ring.

What is claimed is:

1. A method for manufacturing a nano-vesicle holding a target hydrophobic drug comprising:
    (a) refluxing 4-hydroxybenzaldehyde with potassium carbonate and acetone at 80° C. for 40 min;
    (b) adding 1-bromohexadecane to reaction mixture in step (a) and refluxing for 12 hours to produce an organic compound;
    (c) separating and purifying the organic compound in step (b) by column chromatography using n-hexane;
    (d) adding resorcinol, acetic acid and sulfuric acid to the organic compound from step (c) and refluxing for 80° C. for 24 hours;
    (e) cooling the reaction mixture from step (d) in an ice bath to zero degrees centigrade to precipitate an amphiphilic supramolecular macrocycle with four lipophilic tails attached to a hydrophilic head groups;
    (f) filtering and washing the precipitate in step (d) with water and drying the precipitate;
    (g) adding one part cholesterol, two parts of the precipitate from step (e), and a suitable quantity of a target hydrophobic drug in an aqueous medium to instantly form a nano-vesicle containing the target drug.

2. The method of claim 1, where the target hydrophobic drug is amphotericin B.

* * * * *